US00PP20693P3

(12) United States Plant Patent
Hosogai

(10) Patent No.: US PP20,693 P3
(45) Date of Patent: Jan. 26, 2010

(54) ***COREOPSIS* PLANT NAMED 'GOLDEN DREAM'**

(50) Latin Name: *Coreopsis verticillata*
Varietal Denomination: Golden Dream

(75) Inventor: Yohei Hosogai, Niitsu (JP)

(73) Assignee: June Croon, Cutchogue, NY (US)

( * ) Notice: Subject to any disclaimer, the term of this patent is extended or adjusted under 35 U.S.C. 154(b) by 0 days.

(21) Appl. No.: 12/148,170

(22) Filed: Apr. 17, 2008

(65) Prior Publication Data

US 2009/0265821 P1 Oct. 22, 2009

(51) Int. Cl.
*A01H 5/00* (2006.01)

(52) U.S. Cl. ..... Plt./417

(58) Field of Classification Search ..... Plt./417
See application file for complete search history.

*Primary Examiner*—June Hwu
(74) *Attorney, Agent, or Firm*—The Webb Law Firm

(57) ABSTRACT

A new and distinct cultivar of *Coreopsis verticillata* plant named 'Golden Dream' having bright golden-colored flowers and a long flowering period.

2 Drawing Sheets

Botanical classification: *Coreopsis verticillata.*
Varietal denomination: 'Golden Dream'.

BACKGROUND OF THE INVENTION

The present invention comprises a new and distinct cultivar of *Coreopsis verticillata* known by the varietal name 'Golden Dream'. The new variety was discovered and selected by the breeder in a cultivated environment among plants of 'Creme Brulee' (U.S. Plant Pat. No. 16,096). The new variety was discovered in a greenhouse on Nichien Nursery in Niitsu City, Niigata, Japan in 2005 as a naturally-occurring whole plant mutation of 'Creme Brulee'. Asexual reproduction of the new cultivar by cuttings has shown that the unique features of the new variety are stable and reproduced true to type in successive propagations by asexual reproduction.

The new variety is distinguished from *Coreopsis verticillata* 'Zagreb' (unpatented), as 'Golden Dream' is more compact with stronger stems, and the flower color is orange yellow instead of golden yellow.

The following traits have been repeatedly observed to be unique characteristics of 'Golden Dreain' when compared to other *Coreopsis* varieties known to the breeder:

Upright and outwardly spreading growth habit;
Very freely basal branching habit;
Dense foliage;
Very freely flowering habit with numerous inflorescences per plant;
Bright golden-colored ray florets and dark yellow-colored disc florets; and
Long flowering period.

Further, the new variety has similar foliage and flower arrangement to 'Creme Brulee', but has slightly smaller flowers (2.5 cm. vs. 4.5 cm.), a four times longer bloom time, and a more golden color of its flowers.

BRIEF DESCRIPTION OF THE DRAWINGS

The accompanying colored photographic drawings illustrate the new variety, with the colors being as nearly true as is possible to obtain in colored illustrations of this type.

DESCRIPTION OF THE PLANT

Figure 1:
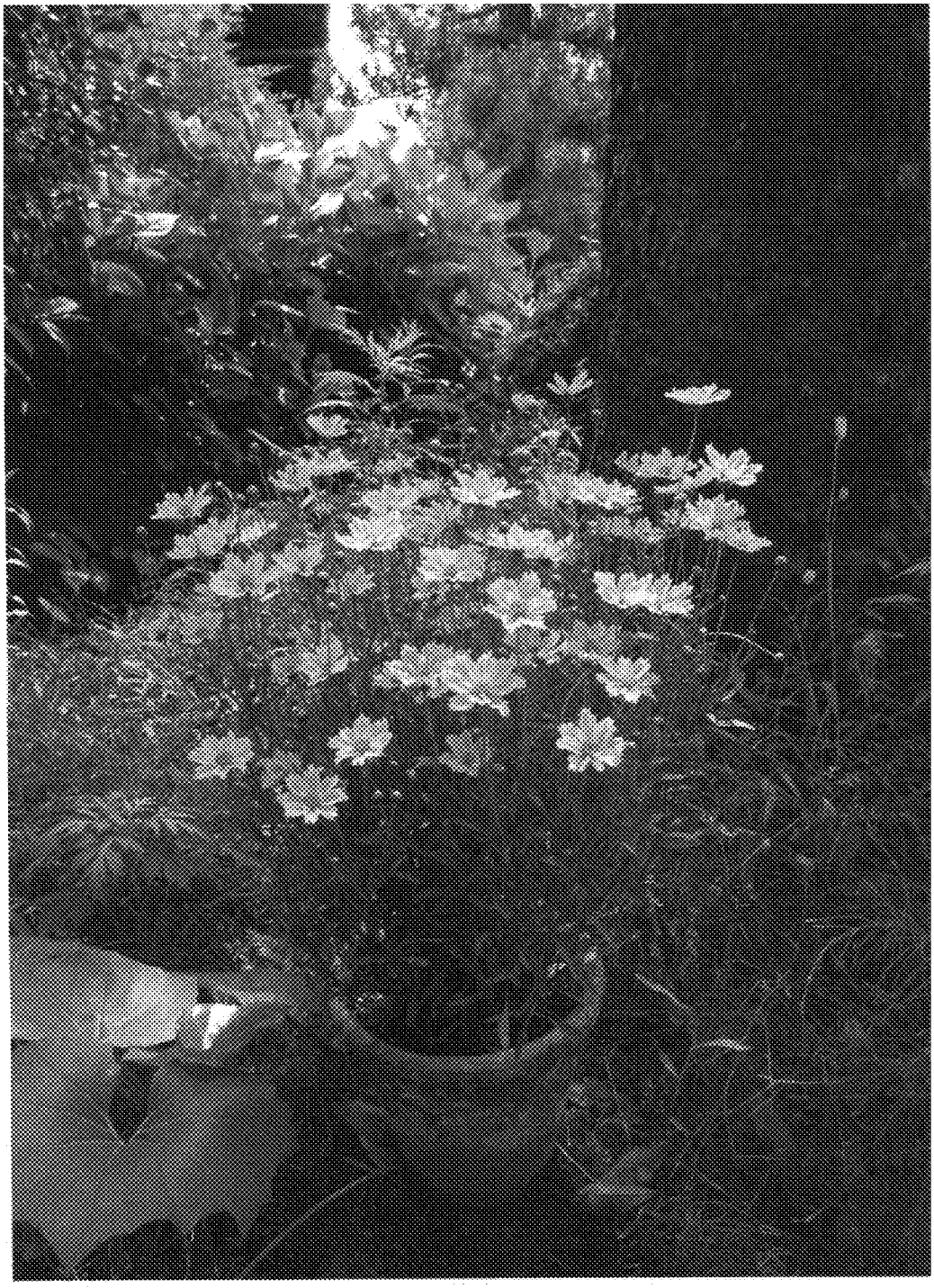
FIG. 1 is a photograph of the entire plant of the new variety.
Figure 2:
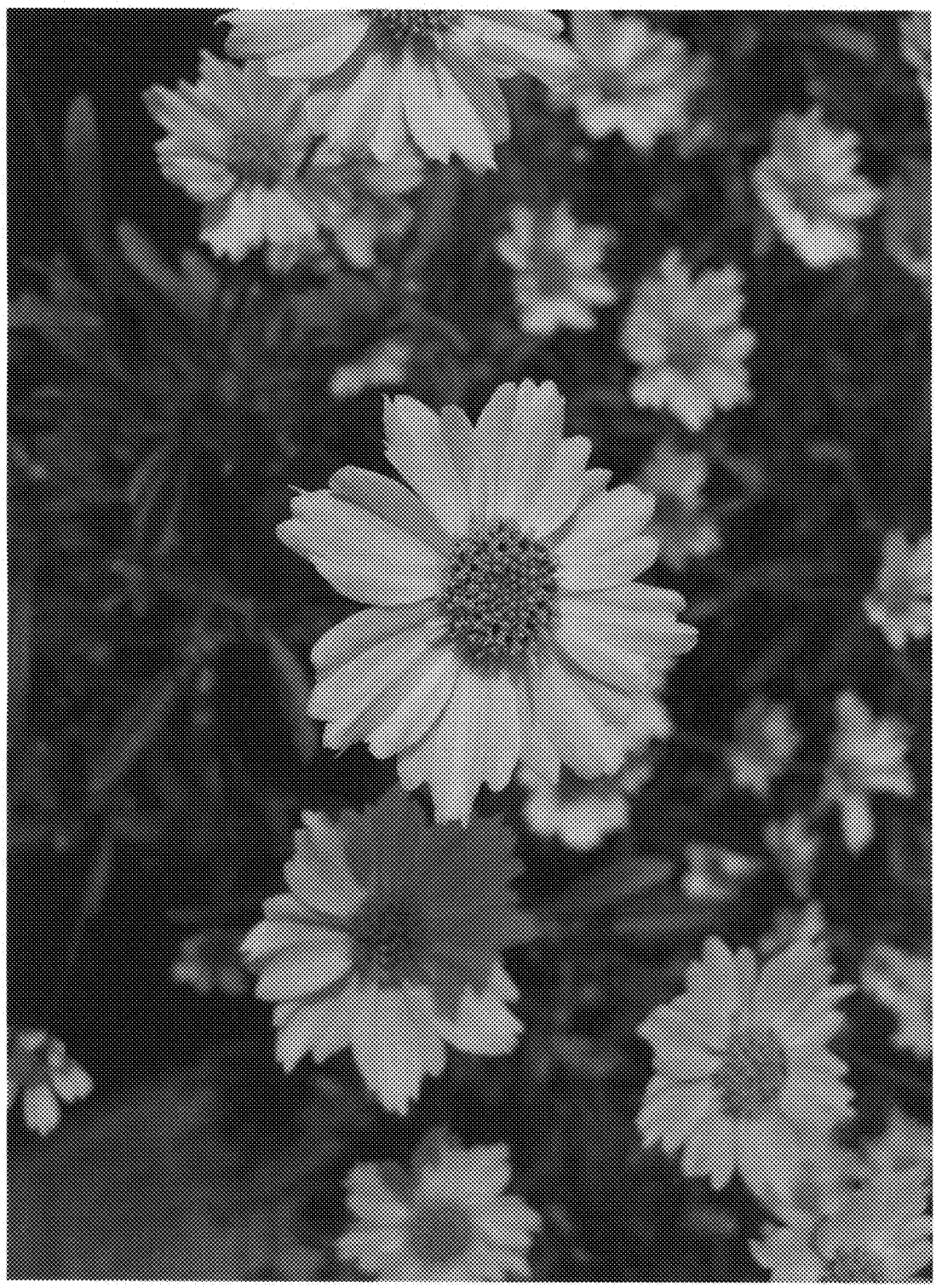
FIG. 2 is a close-up photograph of a flower of the new variety.

The cultivar 'Golden Dreams' has not been observed under all possible environmental conditions. The phenotype may vary somewhat with variations in environment such as temperature, day length and light intensity. However, there is no variance in genotype.

In the following description, color references are made to The Royal Horticultural Society Colour Chart, 2001 Edition, except where general terms of ordinary dictionary significance are used. Plants were asexually reproduced by cuttings and grown and observed in Niitsu City, Niigata, Japan. The plants were grown under natural light in 15 cm. pot containers using a slow-release fertilizer. Some characteristics listed herein were observed on plants grown in Lancaster, Pa. and are identified as such. The plants grown in Lancaster, Pa. were grown under full sun in one gallon containers and were twelve weeks old when described.

PROPAGATION

Time to initiate roots: About 2–3 days at 22° C.
Time to produce a rooted cutting: About 7–10 days at 22° C.
Time to produce a finished flowering plant from a rooted cutting: About 8 weeks in a 10 cm. container.
Root description: Fine and fibrous. Rooting habit: Well-branched.

PLANT AND FOLIAGE DESCRIPTION

General appearance and form: Upright and mounded.
Plant height: 29 cm.
Plant diameter: 30 cm.
Vigor: Excellent.
Branching Habit: Freely basal branching with an average of 2 laterals per node.

Stem:
*Diameter.*—Approximately 2 mm.
*Color.*—Close to 146A.
*Texture.*—Pubescent.
*Pubescence.*—Slight.
Lateral branches:
*Length.*—Primary: Approximately 21 cm. Secondary: Approximately 14 cm.
*Diameter.*—Primary: Approximately 2 mm. Secondary: Approximately 1.5 mm.
*Internode length.*—Approximately 4.6 cm.
*Texture.*—Pubescent.
*Pubescence.*—Slight.
*Color.*—Slightly lighter than 146A.
Foliage:
*Arrangement.*—Alternate.
*Size of leaf.*—Length: Approximately 4.6 cm. Width: Approximately 1.0 cm.
*Shape of leaf* (*generally*).—Narrowly lanceolate to tri-lobed, with deeply dissected lacy appearance
*Shape of apex.*—Acuminate.
*Shape of base.*—Attenuate.
*Texture.*—Upper and lower surfaces slightly pubescent.
*Aspect.*—Horizontal to slightly hanging.
*Margin type.*—Entire.
*Color.*—Young leaves: Upper surface: Close to 147A Lower surface: Close to 146B. Mature leaves: Upper surface: Close to 147A. Lower surface: Close to 146B.
*Petiole.*—Sessile.
*Vein color* (*upper and lower surfaces*).—Close to 147B.

INFLORESCENCE

Bud (evaluated when buds were just opening):
*Shape.*—Globular wine glass.
*Diameter.*—Approximately 7 mm.
*Length.*—Approximately 6 mm.
*Color.*—Approximately 144A.
Natural flowering season: From mid-May in Japan until Autumn
Arrangement: Solitary.
Inflorescence position: Terminally carried on stems arising from leaf axils.
Disc and ray floret arrangement: Disc and ray florets develop acropetally on a capitulum.
Number of inflorescences per lateral branch: Very free flowering with 15 to 20 flowers per lateral branch.
Inflorescence:
*Average size.*—Total width is approximately 2.6 cm.
*Lastingness.*—On a plant, flowers last 5 to 7 days, dependant on ambient temperatures.
Diameter of disc: 0.6 cm.
Lasting quality: Persistent.
Fragrance: None recorded.
Disease resistance: No susceptibility to any disease observed to date.
Insect resistance: No susceptibility to any specific insect observed to date.
Temperature tolerance: Tested in ranges from −12° C. to +35° C.
Drought tolerance: Reasonable to good.

Ray florets:
*Length.*—Approximately 1 cm.
*Width.*—Approximately 0.8 cm.
*Shape.*—Elongated and oblong.
*Apex.*—Emarginate, deeply incised.
*Base.*—Attenuate.
*Margin.*—Entire.
*Aspect.*—Upright.
*Texture.*—The upper surface is smooth and satiny, and the lower surface is smooth.
*Number per inflorescence.*—8.
*Color* (*measured in Lancaster, Pa.*).—When opening: Upper surface: 14B. Lower surface: 12A. Fully opened: Upper surface: A bit brighter than 12A. Lower surface: 12B.
Disc florets:
*Length.*—Approximately 0.7 cm.
*Shape.*—Tubular, flared at apex.
*Number of lobes.*—5 pointed apices.
*Number per inflorescence.*—About 60.
*Color* (*measured in Lancaster, Pa.*).—When opening: Apex: 153C. Mid-section: 164B. Base: 154B. Fully opened: Apex: 153D. Mid-section: 154C. Base: 154D.
Peduncle (data collected in Lancaster, Pa.):
*Length.*—5.8 cm.
*Diameter.*—0.1 cm.
*Aspect.*—Upright or 45° and curling upward.
*Texture.*—Smooth.
*Color.*—138A.

REPRODUCTIVE ORGANS (data collected in Lancaster, Pa.)

Stamen:
*Number.*—Five.
Filament:
*Length.*—0.1 cm.
*Color.*—157A.
Anther:
*Shape.*—Elongate.
*Length.*—0.2 cm.
*Color.*—177A.
Pollen:
*Amount.*—Scarce.
*Color.*—164B.
Pistil:
*Number.*—One per floret—ray and disc.
*Length.*—0.7 cm.
Stigma:
*Shape.*—Bi-partate.
*Color.*—15B.
Style:
*Length.*—0.4 cm.
*Color.*—15D.
Ovary:
*Color.*—154C.
Seeds: None observed to date.

I claim:

1. A new and distinct *Coreopsis verticillata* plant named 'Golden Dream' as is herein described and illustrated.

* * * * *